United States Patent
Jia et al.

(10) Patent No.: US 6,537,563 B2
(45) Date of Patent: Mar. 25, 2003

(54) DENTAL ACID ETCHANT COMPOSITION AND METHOD OF USE

(75) Inventors: Weitao Jia, Wallingford, CT (US); Shuhua Jin, Wallingford, CT (US)

(73) Assignee: Jeneric/Pentron, Inc., Wallingford, CT (US)

( * ) Notice: Subject to any disclaimer, the term of this patent is extended or adjusted under 35 U.S.C. 154(b) by 0 days.

(21) Appl. No.: 09/853,477

(22) Filed: May 11, 2001

(65) Prior Publication Data

US 2002/0018755 A1 Feb. 14, 2002

Related U.S. Application Data

(60) Provisional application No. 60/203,292, filed on May 11, 2000.

(51) Int. Cl.⁷ ............................. A61K 7/16; A61K 7/18; C09K 13/00; C09K 13/02; C09K 13/08
(52) U.S. Cl. ............................. 424/401; 424/49; 424/57; 424/601; 424/724; 514/63; 514/944; 514/951
(58) Field of Search ............................. 424/401, 49, 57, 424/601, 724; 514/63, 944, 951; 252/79.1, 79.2, 79.4, 79.3, 79.5

(56) References Cited

U.S. PATENT DOCUMENTS 4,802,950 A * 2/1989 Croll .......................... 216/101
6,312,667 B1 * 11/2001 Trom et al. ................... 106/35

OTHER PUBLICATIONS

Kuraray, Co., Ltd., Aug. 23, 1983, JP–58038407–B4, 1983:618644 CAPLUS, abstract.*

* cited by examiner

Primary Examiner—Frederick Krass
Assistant Examiner—Clinton Ostrup
(74) Attorney, Agent, or Firm—Ann M. Knab

(57) ABSTRACT

A gel composition for use in etching the surfaces of teeth in preparation for prophylaxis, repair, or restoration, comprising an aqueous solution of an effective quantity of an acid; and a colloidal silica sol, wherein the silica portion of the sol comprises from about 3 to about 20 weight percent of the total etchant composition.

16 Claims, No Drawings

DENTAL ACID ETCHANT COMPOSITION AND METHOD OF USE

CROSS REFERENCE TO RELATED APPLICATIONS

This application claims priority to U.S. Provisional Application No. 60/203,292 filed May 11, 2000 which is hereby incorporated by reference.

FIELD OF THE INVENTION

The present invention is generally directed to compositions and methods for preparing the surfaces of teeth prior to their repair or filling, and in particular to an acid etchant composition and method of use thereof.

BRIEF DESCRIPTION OF THE RELATED ART

In preparing teeth for application of a dental restorative (such as a sealant, filling material, or the like), a common first step is etching the surface to which the dental restorative is to be applied, with an acid etchant. Acid etchants are commonly thought to clean and demineralize dentin and enamel surfaces so as to promote effective bonding of the restorative material.

Conventional acidic etchant solutions are well known, generally comprising phosphoric acid in an amount of about 10% to about 40% by weight phosphoric acid in aqueous solution or in a gel form. Although the use of conventional phosphoric acid etchants has been generally acceptable in practice, a significant drawback of aqueous solutions is that they tend to run upon application, thereby resulting in etching of healthy tooth surfaces. Gel compositions have accordingly been developed, generally comprising hydrocarbon polymers and/or fumed silica as thickening agents. While such gels do not run upon application, many nonetheless tend to be "stringy", rendering precise application more difficult. Gels which are not stringy tend to be bulky or dry, resulting in clogged dispensing tips. There accordingly remains a need in the art for acid etchant compositions which are thixotropic, not stringy, and easy to dispense.

SUMMARY OF THE INVENTION

The above described drawbacks and deficiencies of the prior art are alleviated by an aqueous, acid gel etchant composition comprising an acid, a colloidal silica sol having pearl-like or elongated forms, and an optional organic thickening agent. The acid is preferably phosphoric acid, present in an amount from about 5 to about 50 weight percent of the total composition. The particles of pearl-like colloidal silica sol preferably have diameters in the range from about 10 to about 60 nanometers. The elongated particles of colloidal silica sol have diameters of about 10 nanometers and lengths in the range from about 50 to about 100 nanometers. The silica portion of the sol comprises from about 3 to about 20 weight percent of the total etchant composition. The optional organic thickening agent, for example carboxypolymethylene or polyethylene oxide, is generally present in an amount from about 0.1 to about 3.0 weight percent of the total composition.

In use, the aqueous, acid gel etchant composition is applied to the tooth surface to be restored using conventional methods such as wiping or dispensing through a needle, after which the gel is removed from the surface of the tooth by rinsing with water while the area is aspirated. The surface is then dried with a jet of air, or blotted dry.

Since the present composition is thixotropic and not stringy, the surface of a tooth to be repaired or restored may be precisely etched without injury to the surrounding gum tissue, or destruction of adjacent teeth surfaces, and without enamel fracture or pitting. Since the present composition is further not stringy or dry, the dispensers used may have small lumens (thus facilitating precise placement) without clogging.

DESCRIPTION OF THE PREFERRED EMBODIMENTS

A thixotropic, aqueous acid gel etchant composition comprises an acid, a colloidal silica sol, and an optional organic thickening agent. Use of a colloidal silica sol thickening agent results in a thixotropic composition which is not stringy and which does not run upon application to the tooth surface, yet which is nonetheless liquid enough to not clog dispensers, e.g. needles, having small lumens.

The preferred acid is phosphoric acid, present in an amount effective to provide etching within about 2 minutes, preferably within about 1 minute. Such quantities are generally in the range from about 10 to about 50 weight percent of the total composition. Other suitable acids include mineral acids such as nitric acid, hydrochloric acid, or sulfuric acid, and organic acids such as tartaric acid, maleic acid, itaconic acid, 5-sulfosalicylic acid, propionic acid, citric acid, oxalic acid, or lactic acid. Combinations comprising at least one of the foregoing acids may also be used. Effective quantities of these acids generally provide a pH of around 1, and are readily determined by one of ordinary skill in the art.

Colloidal silica sols consist of microfine particles of silicon dioxide dispersed in water. Such colloids may be obtained by dispersing negatively charged amorphous silica particles in water. In the present composition, the sol particles are "pearl-like" or elongated. The particles of pearl-like colloidal silica sol preferably have diameters in the range from about 10 to about 60 nanometers. Such sols are commercially available from Nissan Chemical, under the tradename SNOWTEX. The diameter of the particles of the "ST-PSM" product are in the range from about 18 to about 22 nanometers, and the diameters of the particles of the "STP-SL" product are in the range of about 40 to about 50 nanometers. The elongated particles of colloidal silica sol preferably have diameters of about 10 nanometers and lengths in the range from about 50 to about 100 nanometers. Elongated, acidic colloidal silica sols are available from Nissan Chemical under the tradename SNOWTEX, product designation "ST-OUR".

The silica portion of the sol comprises from about 3 to about 20 weight percent of the total etchant composition.

Optional organic thickening agents for inclusion in the present compositions are known, including for example carboxymethylcellulose, polyethylene oxide, gum or salts of polyacrylic acids.

The etching compositions may include other components, for example fluoride, dyes such as methylene blue, or antimicrobial agents.

The acid gel etchant compositions are generally formed by providing a concentrated aqueous phosphoric acid solution and adding the colloidal silica sol solution with mixing. The optional organic thickener and/or other components may be added at any time.

In use, the surface to be repaired or restored is treated with the etchant composition for a period of time effective to etch the surface, and yet not damage the tooth. Effective periods of time are readily determined by those of ordinary skill in the art, and are generally less than about one minute. The composition can be dispensed from a conventional push syringe or squeeze bottle, or applied with a brush. Once the surface of the tooth has been treated with the acid gel etchant composition, the tooth is rinsed with water while the area is aspirated and thereafter the area is dried with a jet of air or by blotting. As with conventional acid etch compositions, care should be taken to avoid skin contact or contact with oral mucosa and eyes to prevent possible injury to the patient. Conventional prophylactic, repair and restorative materials are then applied using known methods, for example sealants, primers, primer/adhesives, adhesives, glass ionomer cements, filling materials, and the like.

The following nonlimiting examples illustrate the invention.

EXAMPLE 1

An etching gel was prepared by mixing 50 g of ST-PSM solution (about 20% by weight colloidal silica content) available under the Snowtex product line from Nissan Chemical Industries, Ltd. with 43 g of 85–87% $H_3PO_4$ to make a gel. Seven grams of 4% polyethylene oxide solution were added to the gel to further thicken it. The resultant gel had desirable handling characteristics and was smooth and easy to dispense through a 25 gauge tip.

COMPARATIVE EXAMPLE 2

As a comparison, an etching gel with similar consistency as the gel in Example 1 was prepared. Regular fumed silica, A-200, available from Deggusa Corp. located in Pa., was used as the thickening agent, and mixed with 37% $H_3PO_4$ at 10% by weight. The gel that was produced had a smooth feel, but was difficult to dispense through a 25 gauge tip.

EXAMPLE 3

The following test shows one of the desirable properties associated with the use of colloidal silica as a thickening agent for dental conditioning compositions. Heat accelerated aging tests were conducted for various acid etching compositions as indicated in Table 1 below. Dispensability from 25 gauge needle tips and physical appearance evaluations were performed for the etching gel compositions after exposing the gels to heat at 37° C. for two days in an open container. The experiments were conducted on the new gel formulation of the invention as set forth in Example 1 above, regular fumed silica as set forth in Comparative Example 2 above, and some commercially available etching gels.

TABLE 1

Property comparison of various etching gels after 2 days heat at 37° C.

| Etching Gel | Thickening Agent | Dispensability from 25 Gauge Needle | Physical Appearance |
| --- | --- | --- | --- |
| Example 1 | Nissan silica | easy and controllable | gel |
| Comparative Example 2 | Regular fumed silica | non-dispensable | solid |
| Vivadent Total Etch ™ | unknown | poor dispensability | very thick gel |
| Jeneric/Pentron Etchant (37% $H_3PO_4$) | gum xanthan | easy but runny | watery |
| Bisco All Etch ™ | unknown | easy but runny | watery |

Film thickness and disk diameter were also measured for each etching gel "as is" and after heating them in an oven at 37° C. for two days. The film thickness and disk diameter were measured between two GOLGSEAL™ microslides of 50 by 75 mm size using 0.02 g of each sample under 1 kg load for 1 minute. The test results are shown in Table 2 below.

TABLE 2

Film thickness and disk diameter comparison of various etching gels measured as is and after 2 days heat at 37° C.

| Etching gel ID | Film thickness (µm) | | Disk diameter (mm) | |
| --- | --- | --- | --- | --- |
| | as is | oven aged | as is | oven aged |
| Example 1 | 3 | 10 | 50 | 30 |
| Example 2 | 10 | N/A | 10 | N/A |
| Vivadent Total Etch ™ | 6 | 150 | 30 | 8 |
| J/P Etchant | 8 | 1 | 39 | 45 |
| Bisco All Etch ™ | 7 | 4 | 40 | 45 |

For the new gel formulation of the invention containing Nissan silica, Example 1 above, film thickness increased (or disk diameter decreased) after water loss, but the fold of increase (or decrease) was much less than that of the gel of Comparative Example 2 above and for the Total Etch etchant. The gel of Comparative Example 2 contained regular fumed silica, and dried out easily. Since the gel of Comparative Example 2 was not dispersible at a 1 kg load, its film thickness and disk diameter were not measurable. The Jeneric/Pentron 37% $H_3PO_4$ etchant and the All Etch etchant, however, lost their viscosity after heat treatment, presumably due to the degradation of polymer thickener during the heat aging process.

The foregoing description illustrates preferred embodiments of the invention. However, concepts employed may, based upon such description, be employed in other embodiments without departing from the scope of the invention. Accordingly, the following claims are intended to recite the invention broadly, as well as in the specific forms herein.

What is claimed is:

1. A method of etching the surface of a tooth in preparation for prophylaxis, repair, or restoration, comprising applying to the surface of the tooth an aqueous, acid gel etchant composition comprising
an aqueous solution of an effective quantity of an acid;
a colloidal silica sol, wherein the silica portion of the sol comprises from about 3 to about 20 weight percent of the total etchant composition; and rinsing the acid etchant from the surface of the tooth.

2. The method of claim 1, wherein the acid is phosphoric acid, present in an amount from about 10 to about 50 weight percent of the total composition.

3. The method of claim 1, wherein the acid etchant composition further comprises from about 0.1 to about 3 weight percent of an organic thickener.

4. The method of claim 3, wherein the organic thickener is polyethylene oxide.

5. The method of claim 3 wherein the organic thickener comprises carboxymethylcellulose, or grum or salts of polyacrylic acids.

6. The method of claim 1 in which the acid gel etchant composition is applied to the surface of the tooth for periods between from about 10 to about 60 seconds.

7. The method of claim 1, wherein the colloidal silica sol comprises particles in the range from about 10 to about 60 nanometers 8. The method of claim 1 wherein the acid comprises a mineral acid.

9. The method of claim 8 wherein the mineral acid is selected from the group consisting of nitric acid, hydrochloric acid, sulfuric acid, and mixtures thereof.

10. The method of claim 1 wherein the acid comprises an organic acid.

11. The method of claim 10 wherein the organic acid is selected from the group consisting of tartaric acid, maleic acid, itaconic acid, 5-sulfosalicylic acid propionic acid, citric acid, oxalic acid, lactic acid and mixtures thereof.

12. The method of claim 1 wherein the colloidal silica sol comprises particles having lengths in the range from about 50 to about 100 nanometers.

13. The method of claim 1 wherein the acid etchant composition further comprises fluoride.

14. The method of claim 1 wherein the acid etchant composition further comprises dye.

15. The method of claim 14 wherein the dye comprises methylene blue.

16. The method of claim 1 wherein the acid etchant composition further comprises an antimicrobial agent.

* * * * *